United States Patent [19]
Silvian

[11] Patent Number: 5,769,876
[45] Date of Patent: Jun. 23, 1998

[54] METHOD AND APPARATUS FOR TELEMETERING DATA BIDIRECTIONALLY BETWEEN TWO DEVICES, ONE DEVICE INCORPORATING A COARSE PHASE ADJUSTMENT AND THE OTHER DEVICE INCORPORATING A FINE PHASE ADJUSTMENT

[75] Inventor: Sergiu Silvian, La Crescenta, Calif.

[73] Assignee: Pacesetter, Inc., Sylmar, Calif.

[21] Appl. No.: 674,486

[22] Filed: Jul. 2, 1996

[51] Int. Cl.⁶ .................................................. A61M 1/37
[52] U.S. Cl. .............................. 607/60; 607/32; 128/903
[58] Field of Search ........................ 607/32, 60; 128/903

[56] References Cited

U.S. PATENT DOCUMENTS

| | | | |
|---|---|---|---|
| 4,561,443 | 12/1985 | Hogrefe et al. ........................... | 607/32 |
| 4,681,111 | 7/1987 | Silvian .............................. | 128/419 PT |
| 4,847,617 | 7/1989 | Silvian .............................. | 340/870.16 |
| 4,944,299 | 7/1990 | Silvian .............................. | 128/419 PG |
| 5,058,581 | 10/1991 | Silvian .............................. | 128/419 PG |
| 5,264,843 | 11/1993 | Silvian .............................. | 340/870.18 |
| 5,466,246 | 11/1995 | Silvian ..................................... | 607/32 |
| 5,522,866 | 6/1996 | Fernald ..................................... | 607/60 |
| 5,562,713 | 10/1996 | Silvian ..................................... | 607/32 |
| 5,569,307 | 10/1996 | Schulman et al. ........................ | 607/60 |

*Primary Examiner*—William E. Kamm

[57] ABSTRACT

An improved system is disclosed for telemetering data bidirectionally between two devices such as an implantable device and an external programmer. The two devices both include clock generators that operate at the same nominal frequency, but only one of the devices (i.e., the programmer) includes a phase-locked loop receiver that adjusts the frequency and phase of its clock signal to match that of the received data. The clock generator of the other device (i.e., the implantable device) generates a fixed-phase clock signal, which is selectively inverted or not inverted, to adjust its phase by 180°. This selective 180° adjustment enables the programmer's phase-locked loop receiver to have a reduced, ±90° pull-in range, which simplifies its construction and reduces the time required to achieve synchronization.

21 Claims, 2 Drawing Sheets

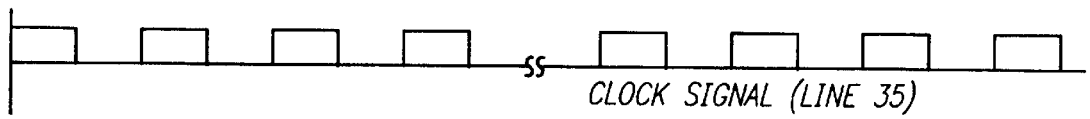
FIG. 3A CLOCK SIGNAL (LINE 35)
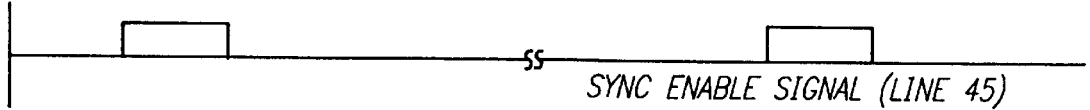
FIG. 3B SYNC ENABLE SIGNAL (LINE 45)
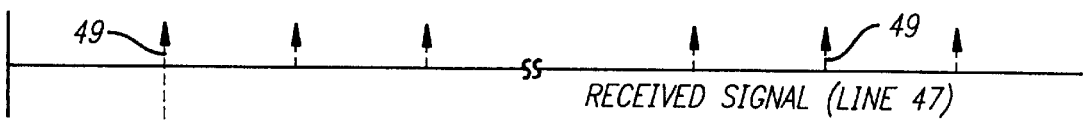
FIG. 3C RECEIVED SIGNAL (LINE 47)
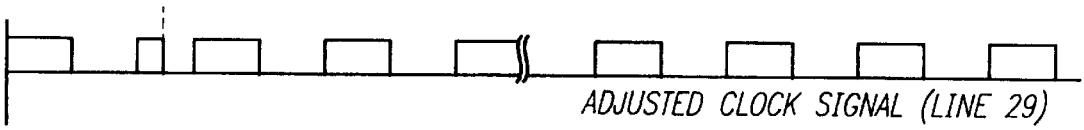
FIG. 3D ADJUSTED CLOCK SIGNAL (LINE 29)

METHOD AND APPARATUS FOR TELEMETERING DATA BIDIRECTIONALLY BETWEEN TWO DEVICES, ONE DEVICE INCORPORATING A COARSE PHASE ADJUSTMENT AND THE OTHER DEVICE INCORPORATING A FINE PHASE ADJUSTMENT

BACKGROUND OF THE INVENTION

This invention relates generally to telemetry systems and, more particularly, to bidirectional telemetry systems that transmit data between two devices in a half-duplex fashion.

Bidirectional telemetry systems of this particular kind are useful, for example, in transmitting data between an implantable device such as a cardiac pacemaker and an external programmer. Typically, such telemetry systems transmit data in a succession of short packets that form data frames of uniform duration, e.g., 8 milliseconds. During a first portion of each frame, the programmer transmits a group of data symbols to the implantable device, and during a second portion of the frame, the implantable device transmits a group of data symbols to the programmer. Brief change-over times separate the successive frames and also separate the first and second portions of each frame. The programmer and the implantable device each transmit and receive data using their own internal clock generators, which generate clock signals having roughly the same nominal frequency.

Because of size and power limitations, the implantable device preferably is implemented without a phase-locked loop for detecting the data received from the external programmer. This can be accomplished by equipping the implantable device with a fixed-phase clock generator (i.e., a master) and by equipping the programmer with a phase-locked loop or similar circuit (i.e., a slave) that tracks the frequency and phase of the implantable device's fixed-phase clock generator. This tracking can ensure that data transmissions in both directions are properly received and detected.

Although the telemetry system described briefly above can operate generally satisfactorily to transmit data bidirectionally between an implantable device and an external programmer, it sometimes can be subject to a 180° phase ambiguity. In particular, the phase-locked loop of the programmer could lock onto the incoming signal received from the implantable device with a phase error of either 0° or 180°. This error could lead to an improper detection of the transmitted data, because it is desirable to sample each symbol at or near its middle.

It should, therefore, be appreciated that there is a need for an improved telemetry system that can reliably transmit data bidirectionally between two devices, such as an implantable device and an external programmer, without the need for a phase-locked loop or similar circuit in one of the devices, and without being subject to any phase ambiguity. The present invention fulfills this and other needs.

SUMMARY OF THE INVENTION

The present invention is embodied in an improved apparatus, and a related method, for telemetering data bidirectionally between two devices, without the need for a phase-locked loop or similar circuit in one of the devices, and without being subject to any phase ambiguity. The two devices, which can take the form of an implantable device and an external programmer, both include clock generators that generate clock signals having roughly the same nominal frequency. A transmitter in the first device (e.g., the programmer) transmits digital data, including a predetermined start signal, based on the first device's clock signal, and a receiver in the second device (e.g., the implantable device) receives that data. A coarse clock phase adjustment circuit in the second device produces an adjusted clock signal that is made to be either substantially in phase with, or substantially out of phase with, the second device's clock signal, depending on the state of that clock signal when the predetermined start signal is received. A transmitter in the second device then transmits data using this adjusted clock signal, and a receiver of the first device receives the data using the first device's clock signal, which will have a maximum phase error of only ±90°.

In a more detailed feature of the invention, the receiver of the first device incorporates a phase-locked loop, with a pull-in range of ±90°. The phase-locked loop detects the symbol rate and phase of the data it receives from the transmitter of the second device, and it controllably adjusts the frequency and phase of the first device's clock signal to correspond to that of the received data.

Further, the clock signal produced by the clock generator of the second device has a fixed phase and is substantially a square wave signal. This enables the coarse clock phase adjustment circuit to function simply by inverting or not inverting the fixed-phase clock signal. The transmitter of the first device transmits the predetermined start signal at regular time intervals and, each time the start signal is received, the coarse clock phase adjustment circuit updates its production of the adjusted clock signal.

Other features and advantages of the present invention should become apparent from the following description of the preferred embodiment, taken in conjunction with the accompanying drawings, which illustrate, by way of example, the principles of the invention.

BRIEF DESCRIPTION OF THE DRAWINGS

FIGS. 3A–3D comprise a timing diagram depicting several exemplary signals present in the clock generator circuit of FIG. 2.

DESCRIPTION OF THE PREFERRED EMBODIMENT

Figure 1:
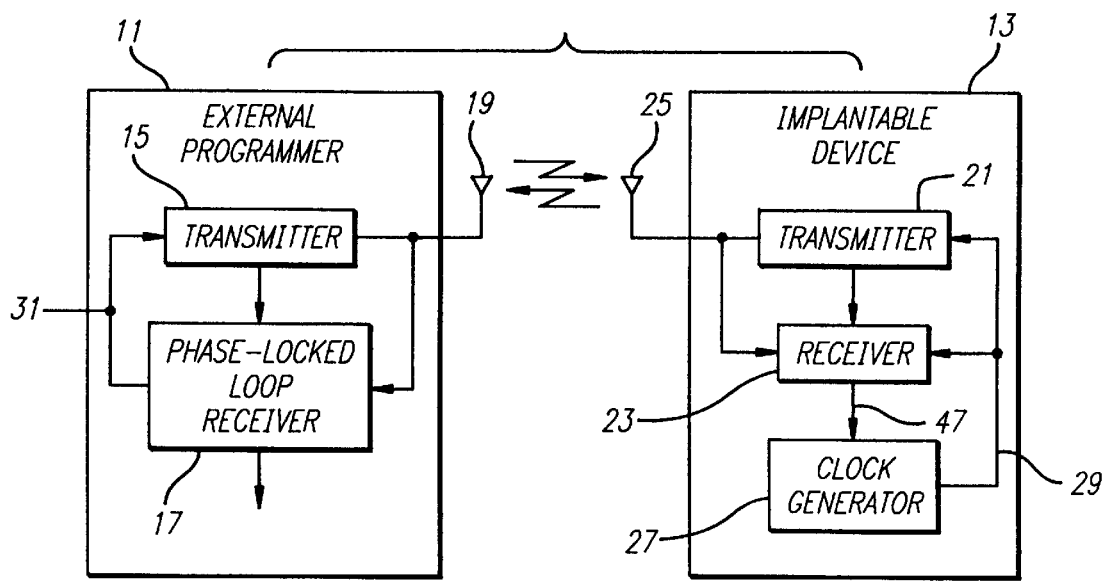
FIG. 1 1 is a simplified block diagram of a telemetry system that communicates data bidirectionally between an implantable device and an external programmer.

With reference now to the drawings, and particularly to FIG. 1, there is shown a half-duplex telemetry system that communicates data bidirectionally between an external programmer 11 and an implantable device 13 such as a cardiac pacemaker. The telemetry system can be used, for example, to recover data accumulated over time by the implantable device, for analysis by a physician, and also to reprogram the implantable device. The programmer is depicted to include a transmitter 15 and a receiver 17, both connected to an antenna 19, and the implantable device similarly is depicted to include a transmitter 21 and a receiver 23, both connected to an antenna 25.

As is conventional, data is communicated bidirectionally between the programmer 11 and the implantable device 13 in packets that form a succession of data frames. Each data frame, which can have a duration of for example 8 milliseconds, includes a first portion, during which the programmer transmits data to the implantable device, and a second portion, during which the implantable device transmits data to the programmer. Brief change-over periods, during which neither the programmer nor the implantable device transmits data, separate the successive data frames and also separate the first and second portions of each frame.

The implantable device 13 further includes a clock generator 27 that outputs a clock signal on line 29, for controlling operation of the device's transmitter 21 and receiver 23. The clock signal, which has a frequency at or near a nominal, but uncontrolled frequency, serves as a master for the communication between the implantable device and the programmer 11.

The receiver 17 of the programmer 11 incorporates a phase-locked loop that tracks the data rate and phase of the data it receives from the implantable device 13. It thus functions as a slave of the implantable device, producing a clock signal having a frequency and phase that match that of the clock signal produced in the implantable device. The programmer's clock signal is used to control the operation of the receiver 17, and it is supplied via line 31 to the programmer's transmitter 15, to control its operation, as well.

Each data frame is initiated by a predetermined start signal transmitted from the programmer 11 to the implantable device 13. The receiver 23 of the implantable device uses a sync enable signal (FIG. 3B) to facilitate its detection of this start signal. This sync enable signal defines a window around the expected arrival time of each successive start signal, based on the time of receipt of the previous start signal and on the known nominal duration of each frame.

Before data is first communicated from the implantable device 13 to the programmer 11, the clock signals of the programmer and the implantable device are not necessarily synchronized with each other in frequency and phase. While data is being communicated from the implantable device to the programmer, however, the programmer's phase-locked loop receiver 17 controllably adjusts the frequency and phase of the programmer's clock signal until the two clock signals are substantially synchronized with each other.

During the first portion of each data frame, when the programmer 11 transmits data to the implantable device 13, the frequency and phase of the two clock signals can drift apart from each other. Immediately thereafter, during the second portion of data frame, when the implantable device transmits data to the programmer, the programmer's phase-locked loop receiver 17 functions to controllably adjust the frequency and phase of the programmer's clock signal to bring the two clock signals back into synchronization.

To achieve the desired clock signal synchronization, the programmer's phase-locked loop receiver 17 could be configured to have a pull-in range of ±180°. However, such a wide range is considered excessive, because it can lead to an excessive synchronization time and because it can unduly complicate the receiver circuitry. In addition, a phase ambiguity between 0° and 180° can arise.

The telemetry system of the invention overcomes this 180° phase ambiguity by configuring the clock generator 27 of the implantable device 13 to selectively adjust the phase of the clock signal on line 29 by 180°, if necessary, at the beginning of each data frame. This selective phase adjustment also ensures that the phase of the implantable device's clock signal will be within ±90° of the phase of the programmer's clock signal, whereby the programmer's phase-locked loop receiver 17 can be configured to have a pull-in range of just ±90°. This can reduce the time required to achieve synchronization and can simplify the receiver circuitry.

Figure 2:
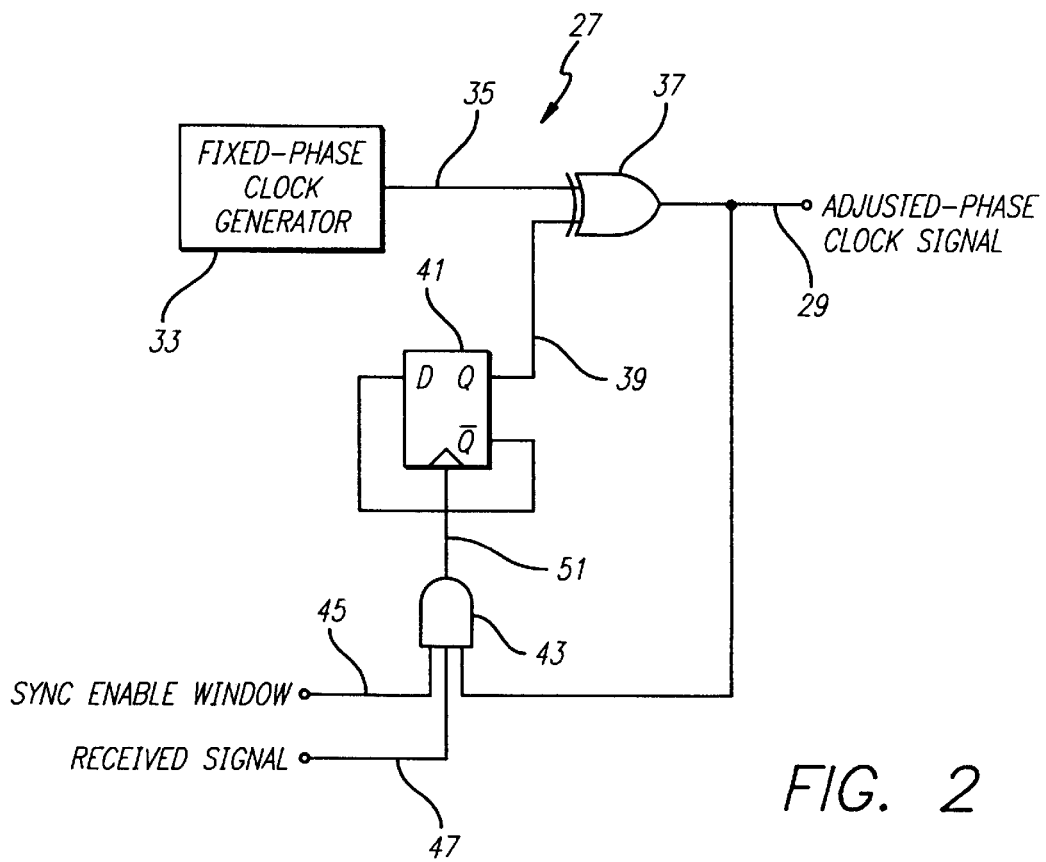
FIG. 2 is a schematic diagram of the clock generator circuit of the implantable device of FIG. 1.

The selective 180° adjustment of the phase of the clock signal output on line 29 by the clock generator 27 of the implantable device 13 is achieved merely by inverting or not inverting a fixed-phase clock signal. A suitable circuit for implementing this clock generator is depicted schematically in FIG. 2. Representative signals present at several locations in the circuit are depicted in FIGS. 3A–3D.

The depicted clock generator 27 includes a fixed-phase clock generator 33 that produces a square-wave clock signal (FIG. 3A) having a nominal frequency corresponding to the desired data transmission rate between the implantable device 13 and the programmer 11. This fixed-phase clock signal is supplied on line 35 to an exclusive-OR gate 37, which produces the adjusted-phase clock signal on line 29 (FIG. 3D). Also supplied to the exclusive-OR gate, via line 39, is a digital control signal output by a flip-flop 41.

The digital control signal supplied on line 39 to the exclusive-OR gate 37 normally remains in one state, high or low, but is made to change its state if it is determined that the phase of the fixed-phase clock signal on line 35 should be inverted. The control signal is produced by the flip-flop 41 in cooperation with an AND gate 43. Three input signals are supplied to the AND gate, including the sync enable signal (FIG. 3B) on line 45, a received signal (FIG. 3C) on line 47, and the adjusted clock signal (FIG. 3D) on line 29. The received signal on line 47 is received from the implantable device's receiver 23, and the first pulse of this signal in each data frame is the start signal, which is identified in FIG. 3C by the reference numeral 49. If all three signals are high, then the AND gate supplies a pulse signal on line 51 to the CLOCK terminal of the flip-flop, which toggles the flip-flop's output signal to its opposite state. Since this output signal is supplied to the exclusive-OR gate 37, this change in state causes a corresponding change in state in the exclusive-OR gate's output signal, i.e., the adjusted clock signal.

Thus, as shown by the representative signals depicted at the left side of FIGS. 3A–3D, the state of the adjusted clock signal on line 29 is made to change if it is high at the time the start signal is received. Conversely, as shown by the signals at the right side of FIGS. 3A–3D, the state of the adjusted clock signal is maintained if it is low at the time the start signal is received. This automatically ensures that the adjusted clock signal has a phase that is within 90° of that of the programmer's clock signal.

It should be appreciated from the foregoing description that the present invention provides an improved system for telemetering data bidirectionally between two devices such as an implantable device and an external programmer. The two devices both include clock generators that operate at the about same nominal frequency, but only one of the devices (i.e., the programmer) includes a phase-locked loop receiver that adjusts the frequency and phase of its clock signal to match that of the received data. The clock generator of the other device (i.e., the implantable device) generates a fixed-phase clock signal, which is selectively inverted or not inverted, to adjust its phase by 180°. This selective 180° adjustment enables the programmer's phase-locked loop receiver to have a reduced, ±90° pull-in range, which reduces the time required to achieve synchronization and simplifies its construction.

Although the invention has been described in detail with reference only to the presently preferred embodiment, those of ordinary skill in the art will appreciate that various modifications can be made without departing from the invention. Accordingly, the invention is defined only by the following claims.

What is claimed is:

1. A method for telemetering data bidirectionally between a first device and a second device, wherein the first device includes a clock generator that generates a first clock signal having a nominal frequency, and wherein the second device includes a clock generator that generates a second clock signal having approximately the same nominal frequency, the second clock signal having a first state and a second state, the method comprising:

transmitting a predetermined start signal from the first device to the second device;

producing at the second device an adjusted clock signal that is substantially in phase with the second clock signal if the second clock signal is in its first state when the start signal is received by the second device, but that is substantially out of phase with the second clock signal if the second clock signal is in its second state when the start signal is received by the second device; and transmitting data from the second device to the first device using the adjusted clock signal.

2. The method, as defined in claim 1, and further comprising detecting the data transmitted from the second device to the first device, using a phase-locked loop receiver having a pull-in range of plus or minus 90°.

3. The method, as defined in claim 1, wherein the second device is implanted within a patient, and the first device is located external to the patient.

4. The method, as defined in claim 1, and further including periodically repeating the steps of transmitting a start signal, producing, and transmitting data.

5. The method, as defined in claim 1, wherein the adjusted clock signal is the same as the second clock signal if the second clock signal is in the first state when the start signal is received by the second device and is the inverse of the second clock signal if the second clock signal is in the second state when the start signal is received by the second device.

6. An apparatus for telemetering data, comprising:

a first device that includes
 a clock generator that generates a first clock signal having a frequency at or near a nominal frequency,
 a transmitter that transmits data, including a start signal, using the first clock signal, and
 a receiver that receives data at a symbol rate at or near the nominal frequency; and a second device that includes
 a clock generator that generates a second clock signal having a first state and a second state and further having a frequency at or near the nominal frequency,
 a receiver that receives data, including the start signal, transmitted by the transmitter of the first device,
 a coarse clock phase adjustment circuit that produces an adjusted clock signal that is substantially in phase with the second clock signal if the second clock signal is in its first state when the start signal is received, but that is substantially out of phase with the second clock signal if the second clock signal is in its second state when the start signal is received, and
 a transmitter that transmits data to the receiver of the first device using the adjusted clock signal.

7. The apparatus, as defined in claim 6, wherein the receiver of the first device incorporates a phase-locked loop having a pull-in range of plus or minus 90°.

8. The apparatus, as defined in claim 6, wherein the receiver of the first device detects the symbol rate and phase of the data it receives from the transmitter of the second device and controllably adjusts the frequency and phase of the first clock signal to correspond to that of the received data.

9. The apparatus, as defined in claim 6, wherein:
the second device is implanted within a patient; and
the first device is located external to the patient.

10. The apparatus, as defined in claim 6, wherein:
the transmitter of the first device transmits the start signal at regular time intervals; and
the coarse clock phase adjustment circuit updates its production of the adjusted clock signal each time the start signal is received.

11. The apparatus, as defined in claim 6, wherein:
the second clock signal, produced by the clock generator of the second device, is substantially a square wave signal; and
the coarse clock phase adjustment circuit produces the adjusted clock signal by duplicating the second clock signal if the second clock signal is in its first state when the start signal is received and by inverting the second clock signal if the second clock signal is in its second state when the start signal is received.

12. A method for telemetering digital information bidirectionally between an external programmer and an implantable device, wherein the programmer includes a clock generator that generates a first clock signal having a nominal frequency, and wherein the implantable device includes a clock generator that generates a second clock signal having substantially the same nominal frequency, the second clock signal having a first state and a second state, the method comprising:

transmitting a predetermined start signal from the programmer to the implantable device;

producing in the implantable device an adjusted clock signal that is the same as the second clock signal if the second clock signal is in the first state when the start signal is received by the implantable device, but that is the inverse of the second clock signal if the second clock signal is in the second state when the start signal is received by the implantable device;

transmitting digital information from the implantable device to the programmer using the adjusted clock signal; and detecting the transmitted digital information.

13. The method, as defined in claim 12, wherein detecting uses a phase-locked loop receiver having a pull-in range of plus or minus 90°.

14. The method, as defined in claim 12, and further including periodically repeating the steps of transmitting a start signal, producing, transmitting digital information, and detecting.

15. An apparatus for telemetering digital information, comprising:

a programmer that includes
 a clock that produces a first clock signal having a frequency at or near a nominal frequency,
 a transmitter that transmits digital information, including a start signal, based on the first clock signal, and
 a receiver that receives digital information at a symbol rate at or near the nominal frequency; and an implantable device that includes
 a clock that produces a second clock signal having a frequency at or near the nominal frequency,
 a receiver that receives digital information transmitted by the transmitter of the programmer, a coarse clock phase adjustment circuit that produces an adjusted clock signal that is the same as the second clock signal if the second clock signal is in a first state when the start signal is received by the receiver of the implantable device, but that is the inverse of the second clock signal if the second clock signal is in the second state when the start signal is received by the receiver of the implantable device, and a transmitter that transmits digital information to the receiver of the programmer based on the adjusted clock signal.

16. The apparatus, as defined in claim 15, wherein the receiver of the programmer incorporates a phase-locked loop receiver with a pull-in range of plus or minus 90°.

17. The apparatus, as defined in claim 15, wherein the receiver of the programmer detects the symbol rate and phase of the digital information it receives from the transmitter of the implantable device and controllably adjusts the frequency and phase of the first clock signal to correspond to that of the received digital information.

18. The apparatus, as defined in claim 15, wherein:

the transmitter of the programmer transmits the start signal at regular time intervals;

the coarse clock phase adjustment circuit updates its production of the adjusted clock signal each time the start signal is received.

19. The apparatus, as defined in claim 15, wherein the second clock signal, produced by the clock of the implantable device, is substantially a square wave signal.

20. A method for telemetering digital information bidirectionally between an external programmer and an implantable device, wherein the programmer includes a clock generator that generates a first clock signal having a nominal frequency, and wherein the implantable device includes a clock generator that generates a second clock signal having substantially the same nominal frequency, the second clock signal alternating between a first state and a second state, the method comprising:

transmitting a predetermined start signal from the programmer to the implantable device;

producing in the implantable device an adjusted clock signal having the same phase as that of the second clock signal if the second clock signal is in the first state when the start signal is received by the implantable device, but that has a phase that differs by a discrete amount from that of the second clock signal if the second clock signal is in the second state when the start signal is received by the implantable device;

transmitting digital information from the implantable device to the programmer using the adjusted clock signal; and detecting the transmitted digital information.

21. The method, as defined in claim 20, wherein:

the second clock signal is substantially a square wave signal;

the adjusted clock signal is substantially the same as the second clock signal if the second clock signal is in the first state when the start signal is received by the implantable device, and is substantially the inverse of the second clock signal if the second clock signal is in the second state when the start signal is received by the implantable device; and detecting uses a phase-locked loop receiver having a pull-in range of plus or minus 90°.

* * * * *